United States Patent
Moszner et al.

(10) Patent No.: US 7,622,538 B2
(45) Date of Patent: Nov. 24, 2009

(54) SELF-ETCHING DENTAL MATERIALS BASED ON (METH) ACRYLAMIDE PHOSPHATES

(75) Inventors: Norbert Moszner, Eschen (LI); Iris Lamparth, Grabs (CH); Frank Zeuner, Vaduz (LI); Ulrich Salz, Lindau (DE); Angela Mucke, Schlins (AT); Jorg Zimmermann, Lustenau (AT); Jorg Angermann, Feldkirch (AT); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 189 days.

(21) Appl. No.: 11/211,938

(22) Filed: Aug. 25, 2005

(65) Prior Publication Data
US 2006/0135719 A1 Jun. 22, 2006

(30) Foreign Application Priority Data
Dec. 22, 2004 (DE) .............. 10 2004 061 925

(51) Int. Cl.
C08F 20/58 (2006.01)
C08F 20/60 (2006.01)

(52) U.S. Cl. ............... 526/307; 526/263; 526/265; 526/277; 526/304; 526/305; 526/307.2; 526/307.3; 526/307.5; 526/307.6; 526/307.7; 526/306

(58) Field of Classification Search ......... 526/263, 526/265, 277, 304, 305, 306, 307.2, 307.3, 526/307.5, 307.6, 307.7, 307
See application file for complete search history.

(56) References Cited

U.S. PATENT DOCUMENTS

| | | | | |
|---|---|---|---|---|
| 5,055,497 A * | 10/1991 | Okada et al. | | 523/116 |
| 6,759,449 B2 * | 7/2004 | Kimura et al. | | 523/118 |
| 7,041,714 B2 * | 5/2006 | Takeshita et al. | | 523/118 |
| 7,449,499 B2 * | 11/2008 | Craig et al. | | 523/118 |
| 2004/0192805 A1 | 9/2004 | Finger | | |
| 2004/0266906 A1 * | 12/2004 | Klee et al. | | 523/118 |

FOREIGN PATENT DOCUMENTS

| EP | 0 333 503 | 8/1989 |
|---|---|---|
| EP | 0 712 622 | 5/1996 |
| EP | 1 249 221 | 10/2002 |
| EP | 1 459 726 | 9/2004 |

OTHER PUBLICATIONS

Gaj & Moore, "Substituted 1-Alkyl-3-Azetidinols," *Tetrahedron Lett.* 23:2155-2157 (1967).
Houben-Weyl, "Methoden der Organischen Chemie," Georg Thieme Verlag, New York, vol. E5, pp. 941-966 (1985).
Xu & Prestwich, "Concise Synthesis of Acyl Migration-Blocked 1,1-Difluorinated Analogues of Lysophosphatidic Acid," *J. Org. Chem.* 67:7158-7161(2002).
German Office Action dated Nov. 24, 2008.

\* cited by examiner

*Primary Examiner*—Helen L. Pezzuto
(74) *Attorney, Agent, or Firm*—Nixon Peabody LLP

(57) ABSTRACT

Polymerizable dental material, characterized in that it contains at least one (meth)acrylamide phosphate of the following general formula (I):

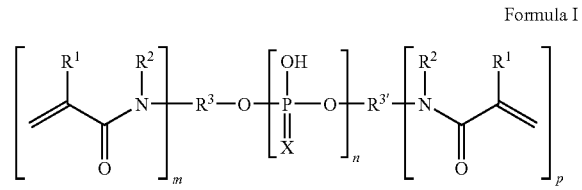

Formula I in which $R^1$ is H or $CH_3$; $R^2$ is H or a $C_1$-$C_4$ alkyl radical or forms together with the nitrogen atom to which it is bonded and one or more atoms which belong to $R^3$ or $R^{3'}$ a heterocyclic ring; $R^3$, $R^{3'}$ independently of each other are a linear or branched aliphatic $C_1$-$C_{50}$ radical with a valency of m+n or p+n, an aromatic $C_6$-$C_{18}$ radical with a valency of m+n or p+n, or a cycloaliphatic, araliphatic or heterocyclic $C_3$-$C_{18}$ radical with a valency of m+n or p+n, wherein the carbon chains of the radical or radicals can be interrupted by O, S, $CONR^4$, OCONH, or form together with one or more atoms which belong to $R^2$ and the nitrogen atom, to which the $R^2$ is bonded a heterocyclic ring, $R^{3t}$ being H if p=0, and $R^4$ being H, $C_1$-$C_{10}$ alkyl, $C_6$-$C_{12}$ aryl, $C_6$-$C_{10}$ aralkyl or a bicylic $C_4$-$C_{12}$ radial; n is 1, 2, 3 or 4 if p=0, and is 1 or 2 if p ≠0; m is 1, 2, 3 or 4; p is 0, 1, 2, 3 or 4; x is O or S.

11 Claims, No Drawings

SELF-ETCHING DENTAL MATERIALS BASED ON (METH) ACRYLAMIDE PHOSPHATES

The present invention relates to (meth)acrylamide phosphates with a high hydrolysis resistance which are suitable in particular as adhesion component for self-etching dental materials such as adhesives, coating materials and composites.

Nowadays self-etching, self-conditioning dentine-enamel adhesives are increasingly used in restorative dentistry. These adhesives are mostly constructed such that they contain an adhesion monomer with acid function, one or more non-acid comonomers, solvent, a polymerization initiator and optionally further additives. Suitable as polymerizable adhesion monomers are above all acid monomers which on the one hand exhibit a high reactivity during radical polymerization and on the other hand are capable of conditioning the hard tooth substance sufficiently rapidly. Known examples of such acid monomers are carboxylic acid methacrylates, such as 4-MET (4-methacryloyloxyethyloxycarbonyl phthalic acid), MAC-10 (10-methacryloyloxydecyl malonic acid) or acid methacrylate phosphates, such as MDP (10-methacryloyloxydecyl dihydrogen phosphate) or MEP (2-methacryloyloxyethyl dihydrogen phosphate):

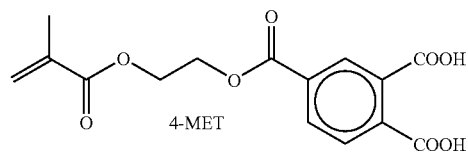
4-MET

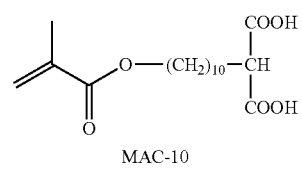
MAC-10

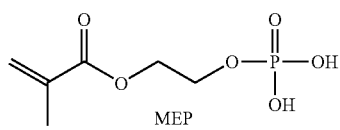
MEP

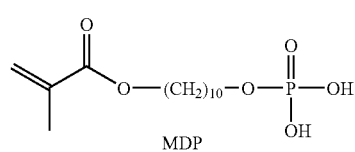
MDP

In this connection acid dimethacrylates are also known which, like PMDM (addition product of 1 mol of pyromellitic acid anhydride with 2 mol of 2-hydroxyethyl methacrylate) or GDMP [(1,3-dimethacryloyloxy)-prop-2-yl-dihydrogen phosphate], are characterized, because of their cross-linking properties, by a high polymerization activity:

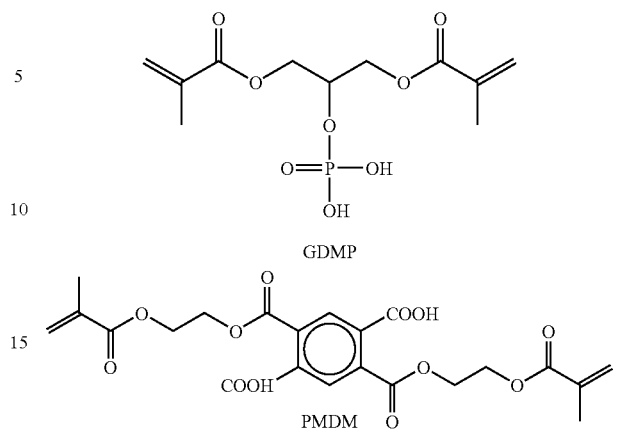

Water is used in most cases as solvent or co-solvent in enamel-dentine adhesives, as it promotes the wetting of the hard tooth substance. The ester bonds of the methacrylates are however known to be hydrolyzed under acid, aqueous conditions. Through the hydrolysis of the monomers, the corresponding adhesive loses its function, and the adhesion effect clearly decreases over time. Therefore the acid monomers are stored water-free and mostly separate from the other adhesive constituents. They are either mixed shortly before use with the aqueous part or applied separately to the tooth surface. It would be of great advantage if hydrolysis-stable adhesives could be prepared which combine all the components in one composition.

Hydrolysis-stable acryl phosphonic acids are known from EP 0 909 761 A1 and DE 102 34 326 in which polymerizable (meth)acryl groups are bonded to the radical of the molecule via ether-, thioether-, or via carbon-carbon bonds.

EP 1 169 996 A1 discloses dental materials based on (meth)acrylamide phosphonic acids which, because of a relatively long-chain bridge between phosphonic acid group and reactive double bond, are said to have a high hydrolysis stability and improved adhesion properties.

WO 03/035013 and WO 03/013444 disclose self-etching, self-conditioning dental adhesives based on (meth)acrylamides containing acid groups, with monomers containing sulfonic acid and phosphonic acid groups being preferred. These compounds can be obtained synthetically only with difficulty.

Curable compositions are known from DE 0 333 503 A2 which contain filler which has been treated with polymerizable organic phosphoric- or phosphonic acid compounds. The compositions can additionally contain acid monomers.

The object of the invention is to provide a dental material which can be cured by means of radical polymerization, at the same time showing a high polymerization tendency, which is insensitive to hydrolysis in the presence of water at room temperature and is thus storage-stable and capable of etching the hard tooth substance.

The object is achieved according to the invention by polymerizable dental materials which contain at least one (meth)acrylamide phosphate of the following general formula (I) or a pyrophosphate thereof:

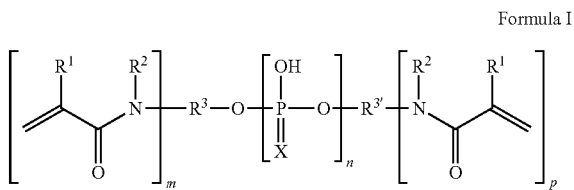

Formula I in which
R$^1$ is H or CH$_3$;
R$^2$ is H or a C$_1$-C$_4$ alkyl radical or forms together with the nitrogen atom to which it is bonded and one or more atoms which belong to R$^3$ or R$^{3'}$ a heterocyclic ring;
R$^3$, R$^{3'}$ independently of each other are a linear or branched aliphatic C$_1$-C$_{50}$ radical with a valency of m+n or p+n, an aromatic C$_6$-C$_{18}$ radical with a valency of m+n or p+n, or a cycloaliphatic, araliphatic or heterocyclic C$_3$-C$_{18}$ radical with a valency of m+n or p+n, wherein the carbon chains of the radical or radicals can be interrupted by O, S, CONR$^4$, OCONH, or form together with one or more atoms which belong to R$^2$ and the nitrogen atom to which R$^2$ is bonded a heterocyclic ring, R$^{3'}$ being H if p=0, and wherein
R$^4$ is H, C$_1$-C$_{10}$ alkyl, C$_6$-C$_{12}$ aryl, C$_6$-C$_{10}$ aralkyl or a bicyclic C$_4$-C$_{12}$ radical;
n is 1, 2, 3 or 4 if p=0, and
is 1 or 2 if p ≠0;
m is 1, 2, 3 or 4;
P is 0, 1, 2, 3 or 4;
x is 0 or S.
R$^2$ is preferably different from H.

By araliphatic or aralkyl radicals is meant groups which contain both aromatic and aliphatic radicals. A typical example of an araliphatic radical is the benzylene radical -Ph-CH$_2$— which comprises an aromatic phenylene group and an aliphatic methylene radical.

By carbon chain which is interrupted by other groups and/or atoms is to be understood that these other groups or atoms are inserted into the carbon chain, i.e. are bonded by carbon atoms on both sides. These groups or atoms cannot therefore assume a terminal position. If several groups or atoms are integrated into a carbon chain, they must in each case be separated from one another by at least one carbon atom. "Carbon chain" does not mean cyclic molecule groups. The total number of groups and/or atoms which are integrated into the carbon chain is smaller by at least the value 1 than the number of carbon atoms in the chain.

The variables of the above formula (I) can have the following preferred meanings independently of one another:
R$^1$=H and/or CH$_3$, wherein in the case m>1 the R$^1$ radicals can have different meanings;
R$^2$=H or a C$_1$-C$_{20}$ alkyl radical or R$^2$ forms together with the nitrogen atom to which it is bonded and one or more atoms which belong to R$^3$ or R$^{3'}$ a heterocyclic ring, preferably a ring with one nitrogen atom and 4 to 7 carbon atoms, in particular a piperidinyl ring;
R$^3$, R$^{3'}$=independently of each other a linear or branched aliphatic C$_1$-C$_{10}$ radical with a valency of m+n or n+p, an aromatic C$_6$-C$_{10}$ radical with a valency of m+n or n+p, or a cycloaliphatic C$_5$-C$_8$ radical or a aralphatic C$_6$-C$_{12}$ radical with a valency of m+n or n+p, wherein the carbon chains of the radical or radicals can be interrupted by O, or R$^3$ and/or R$^{3'}$ form together with one or more atoms which belong to R$^2$ and the nitrogen atom to which R$^2$ is bonded a hetero-cyclic ring, preferably a ring with one nitrogen atom and 4 to 7 carbon atoms, in particular a piperidinyl ring, R$^{3'}$ being H if p=0;
R$^4$=H, C$_1$-C$_6$ alkyl, C$_6$ aryl;
n=1 or 2 if p=0, and
=1 if p≠0;
m=1 or 2;
P=0, 1 or 2;
x=0.

Quite particularly preferred meanings of the variables of the above formula (I) are:
R$^1$=H or CH$_3$;
R$^2$=H or a C$_1$-C$_3$ alkyl radical or R$^2$ forms together with the nitrogen atom to which it is bonded and one or more atoms which belong to R$^3$ a piperidinyl ring;
R$^3$=a linear or branched aliphatic C$_1$-C$_3$ radical with a valency of m+n, or R$^3$ forms together with one or more atoms which belong to R$^2$ and the nitrogen atom to which R$^2$ is bonded a piperidinyl ring, quite particularly preferably a C$_3$ alkylene radical;
R$^{3'}$=H;
R$^4$=H, C$_1$-C$_3$ alkyl;
n=1;
m=1 or 2;
p=0;
x=0.

Compounds of formula (I), in which several and in particular all variables have one of the preferred and in particular of the particularly preferred meanings are particularly suitable according to the invention.

The (meth)acrylamide phosphates according to the invention of general formula (I) (p=0; R$^{3'}$=H; n=1) can for example be prepared in 3 stages starting from reactive (meth)acrylic acid derivatives (chloride, anhydride, ester, acid) and aminoalkanols. Reactive (meth)acrylic acid derivatives and monoaminoalkanols are commercially available. Polyaminoalcohols (m>1, R$^2$=alkyl, aryl etc.) are obtained e.g. by reaction of polyhalogen alcohols with a large excess of an aliphatic or aromatic amine (B. J. Gaj and D. R. Moore, Tetrahedron Lett. 23 (1967) 2155).

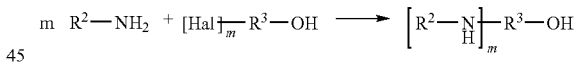

Specific Example:

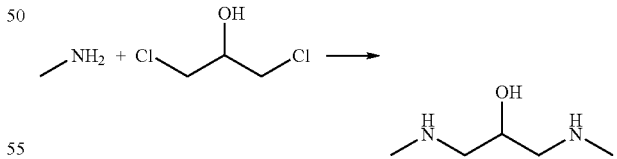

Moreover, diaminoalcohols (m=2, n=1, R$^2$=alkyl, aryl etc.) can be obtained by reaction of aliphatic or aromatic amines with epichlorohydrin (B. J. Gaj and D. R. Moore, Tetrahedron Lett. 23 (1967) 2155).

Specific Example:

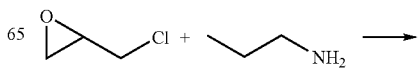

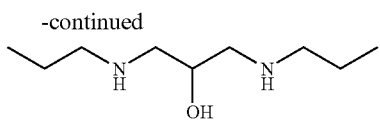

A possibility for the preparation of polyaminopolyols (m,n>1) is the reaction of polyamines with epoxides.

Specific Example:

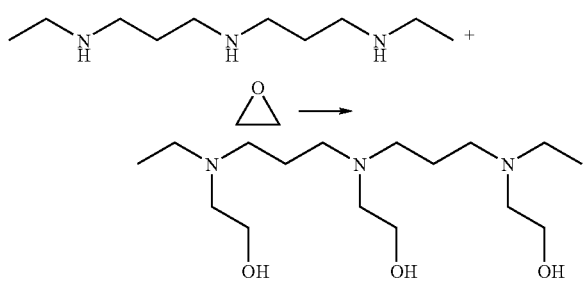

In the 1st reaction stage a reactive (meth)acrylic acid derivative ($R^1$=H, $CH_3$; R'=Hal, O—CO—$CR^1$=$CH_2$, Oalkyl, OH) is reacted with aminoalkanols using the methods known from organic chemistry for the linking of amide bonds (cf. Methoden der Organischen Chemie, HOUBEN-WEYL Volume E5 1985, Georg Thieme Verlag pages 941 ff.) to produce (meth)acrylamidoalcohols.

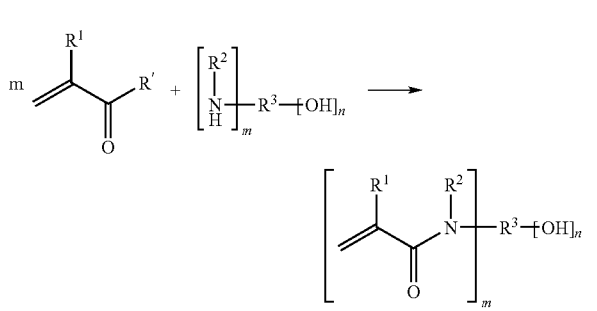

For this purpose in the case m=n=1 the reactive (meth) acrylic acid derivative is reacted with primary ($R^2$=H) or secondary ($R^2$=alkyl, aryl) monoaminoalkanols, in the case m>1, n=1 with primary ($R^2$=H) or secondary ($R^2$=alkyl, aryl) polyaminoalkanols, in the case m=1, n>1 with primary ($R^2$=H) or secondary ($R^2$=alkyl, aryl) aminopolyols and in the case m>1, n>1 with primary ($R^2$=H) or secondary ($R^2$=alkyl, aryl) polyaminopolyols.

The corresponding acid chlorides are preferably used in the presence of equimolar quantities of base.

Specific Example:

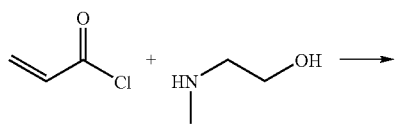

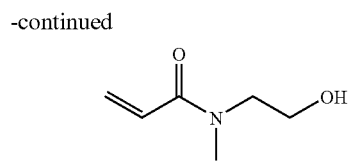

In the 2nd stage the (meth)acrylamidoalcohols are reacted with n equivalents of a phosphoryl compound, preferably dimethyl chlorophosphate ($R^5$=$CH_3$) (Y. Xu., G. D. Prestwich, J. Org. Chem. 67 (2002) 7158).

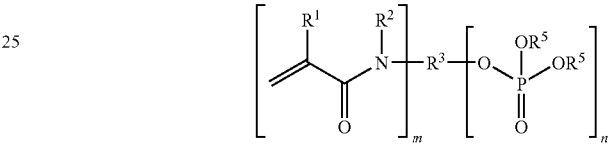

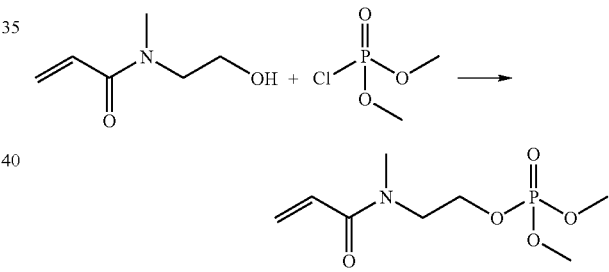

Specific Example:

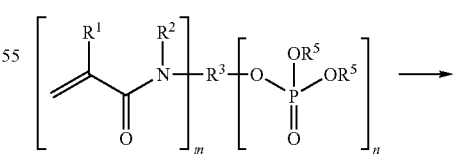

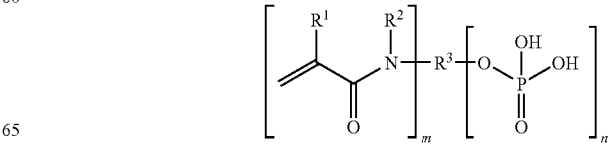

In the 3rd stage the selective hydrolysis of the alkoxy groups $OR^5$ takes place, a dimethyl phosphate ($R^5$=$CH_3$) preferably being used in which the splitting-off is carried out with bromotrimethylsilane (Y. Xu., G. D. Prestwich, J. Org. Chem. 67 (2002) 7158).

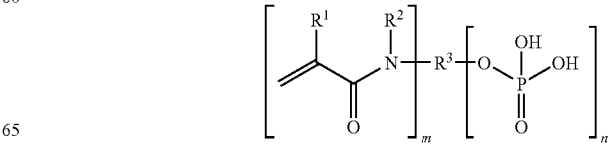

Specific Example:
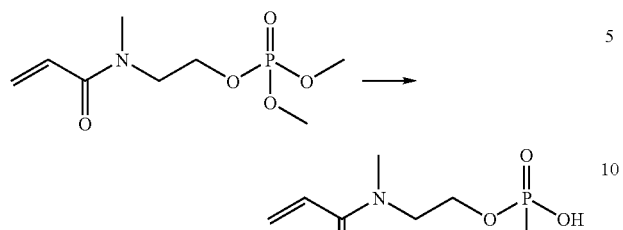
Preferred examples of the (meth)acrylamide phosphates according to the invention of the formula (I) are:
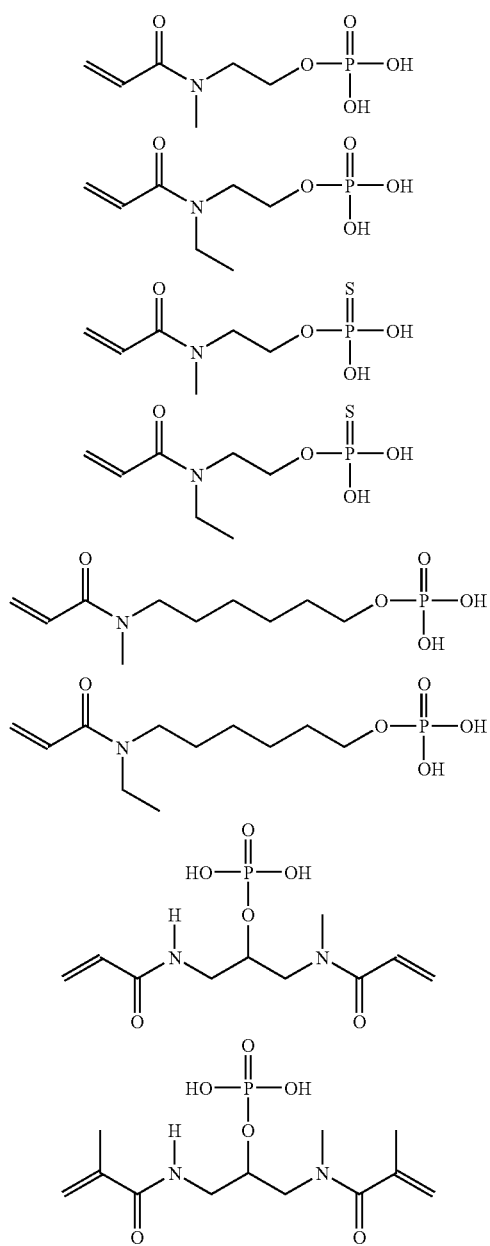
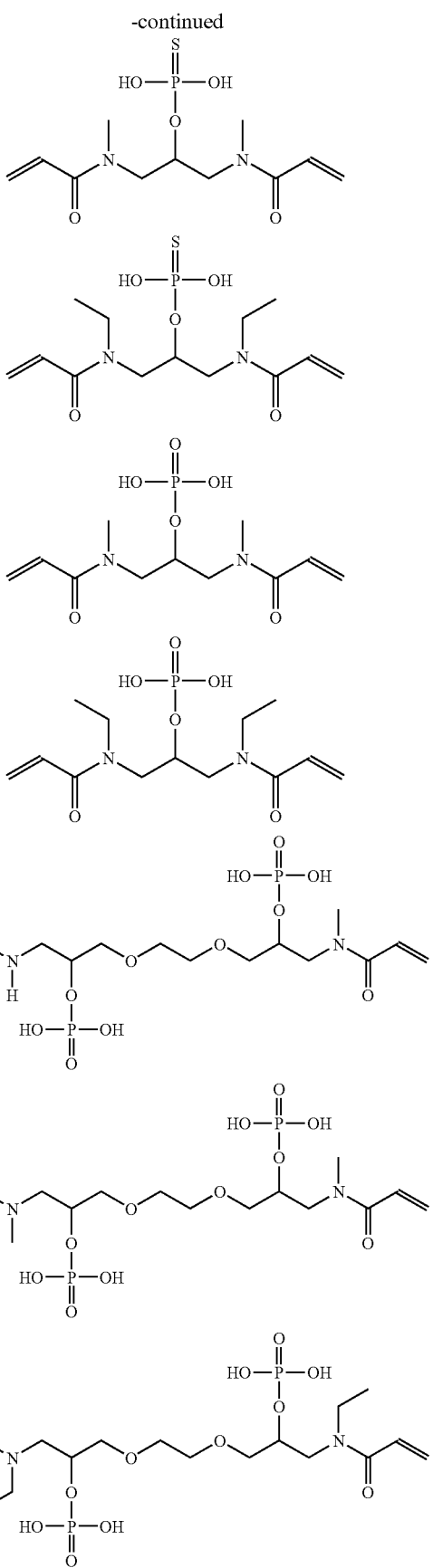

-continued

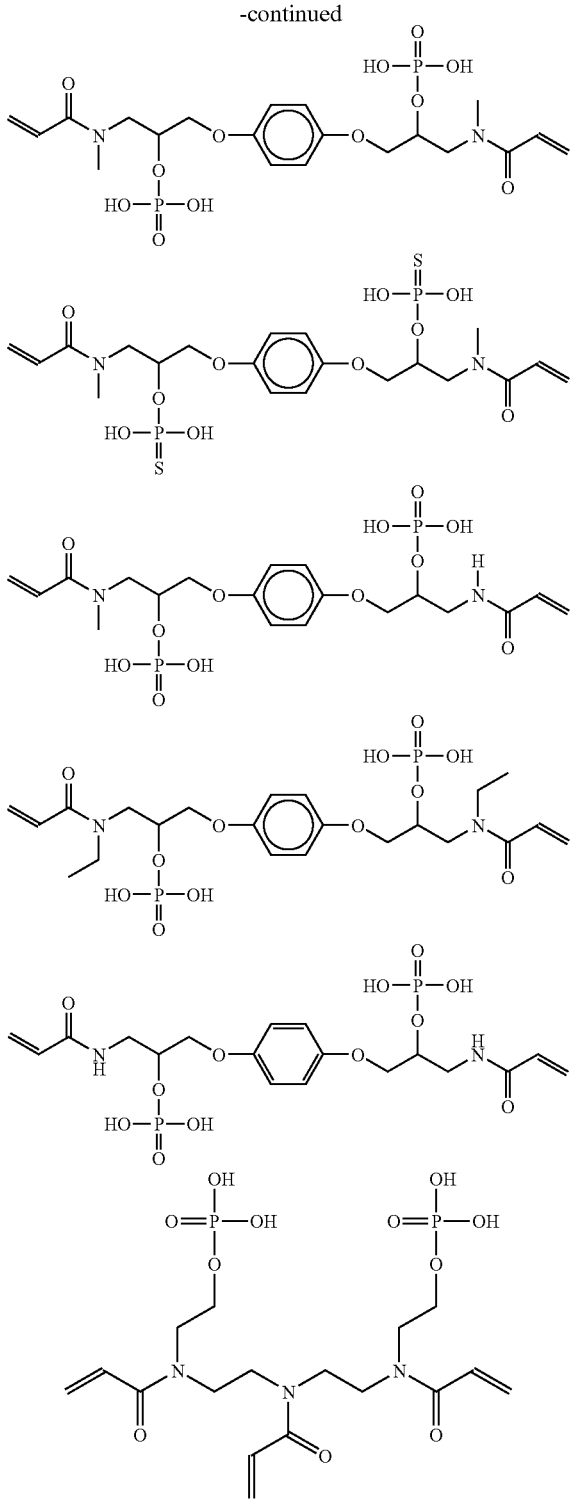

The (meth)acrylamide phosphates according to the invention of formula (I) are strongly acid and very well soluble in water or mixtures of water with polar solvents, such as acetone, ethanol, acetonitrile or tetrahydrofuran (THF). They are capable of etching enamel and dentine comparably with phosphoric acid.

The (meth)acrylamide phosphates of formula (I) are hydrolysis-stable under aqueously acid conditions at room temperature over a long period. In the context of the present invention compounds are described as hydrolysis-stable which are stable in water or in mixtures of water and water-miscible solvents at a concentration of approximately 20 wt.-% and a pH value of approximately 2.0 at 37° C. for at least 6 weeks, i.e. hydrolyze less than 10%, preferably less than 5%.

Because of the high hydrolysis stability of the (meth)acrylamide phosphates according to the invention, mixtures with water and other hydrolysis-stable components can be prepared therefrom which are storage-stable at room temperature. These mixtures show, depending on the structure and concentration of the (meth)acrylamide phosphates of formula (I), a pH value which lies between approximately 0.5 and 3.0 and are therefore capable of etching the surface of the hard tooth substance (enamel and dentine). These mixtures are therefore suitable in particular as adhesives or cements for the dental field, quite particularly as self-etching enamel-dentine adhesives. (Meth)acrylamide phosphates which contain three (m+p=3) and quite particularly preferably two polymerizable (meth)acrylamide groups (m+p=2) are particularly advantageous.

The dental materials according to the invention preferably also contain in addition to the (meth)acrylamide phosphates of formula (I) a solvent, particularly preferably water or a mixture of water and a water-miscible solvent. Preferred water-miscible solvents are polar solvents such as acetone, ethanol, acetonitrile, tetrahydrofuran (THF) and mixtures thereof.

Moreover, the dental materials according to the invention can also contain one or more non-acid, radically polymerizable monomers, such as mono- or preferably multi-functional (meth)acryl compounds. By mono-functional (meth)acryl compounds is meant compounds with one, by multi-functional (meth)acryl compounds, compounds with two or more, preferably 2 to 3 (meth)acryl groups.

Preferred monofunctional (meth)acryl compounds are hydrolysis-stable mono(meth)acrylates, e.g. mesityl (meth)acrylate, or 2-(alkoxymethyl) acrylic acids, e.g. 2-(ethoxymethyl)acrylic acid, 2-(hydroxymethyl)acrylic acid, N-mono or N-disubstituted acrylamides, such as e.g. N-ethylacrylamide, N, N-dimethylacrylamide, N-(2-hydroxyethyl)acrylamide or N-methyl-N-(2-hydroxyethyl)acrylamide, N-mono-substituted methacrylamides, such as e.g. N-ethylmethacrylamide or N-(2-hydroxyethyl)methacrylamide, and also N-vinylpyrrolidone or allyl ethers and mixtures of these substances. The above-named monomers are liquid at room temperature or low-melting, i.e. they have a melting point of less than 60° C., and can therefore be used as diluents.

Preferred multi-functional (meth)acrylates are e.g. hydrolysis-stable urethanes from 2-(hydroxymethyl)acrylic acid and diisocyanates, such as 2,2,4-trimethylhexamethylene diisocyanate or isophorone diisocyanate, cross-linking pyrrolidones, such as e.g. 1,6-bis(3-vinyl-2-pyrrolidonyl)-hexane, or bisacrylamides, such as methylene or ethylene bisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction from the corresponding diamines with (meth)acrylic acid chloride. The remaining compounds are mostly commercially available. Multi-functional (meth)acrylates act as cross-linkers during polymerization because of the number of polymerizable groups. Mixtures of these substances and mixtures with monofunctional (meth)acrylates are also suitable.

In order to initiate the radical polymerization the dental materials preferably contain an initiator, particularly preferably a photoinitiator.

Benzophenone, benzoin and their derivatives or α-diketones or their derivatives such as 9,10-phenanthrenequinone, 1-phenyl-propan-1,2-dione, diacetyl or 4,4-dichlorobenzil are preferably used as photoinitiators. Camphorquinone and 2,2-methoxy-2-phenyl-acetophenone and in particular α-diketones are particularly preferably used in combination with amines as reductants, such as e.g. 4-(dimethylamino)-benzoic acid esters, N,N-dimethylaminoethylmethacrylate, N, N-dimethyl-sym.-xylidine or triethanolamine.

Redox-initiator combinations, such as e.g. combinations of benzoylperoxide with N,N-dimethylsym.-xylidine or N,N-dimethyl-p-toluidine are used as initiators for a polymerization carried out at room temperature. In addition, redox systems consisting of peroxides and reductants such as e.g. ascorbic acid, barbiturates or sulfinic acids are also particularly suitable.

Moreover, the dental materials according to the invention can be filled with organic or inorganic particles in order to improve the mechanical properties or adjust the viscosity. Preferred inorganic particulate fillers are amorphous spherical oxide-based materials, such as $ZrO_2$ and $TiO_2$ as well as mixed oxides of $SiO_2$, $ZrO_2$ and/or $TiO_2$, nanoparticulate or microfine fillers, such as pyrogenic silicic acid or precipitation silicic acid as well as minifillers, such as quartz, glass ceramic or glass powder with an average particle size of 0.01 to 1 μm and X-ray-opaque fillers, such as ytterbium trifluoride or nanoparticulate tantalum (V)-oxide or barium sulfate.

Dental materials for use as enamel-dentine adhesives preferably contain as fillers nanoparticulate (primary particle diameters from 1 to 100 nm) amorphous spherical materials based on oxides, such as $ZrO_2$ and $TiO_2$ or mixed oxides of $SiO_2$, pyrogenic silicic acid or precipitated silica, $ZrO_2$ and/or $TiO_2$ and also X-ray-opaque nanoparticulate fillers, such as ytterbium trifluoride, tantalum (V)-oxide or barium sulfate.

In order to obtain the self-conditioning effect of the (meth) acrylamide phosphates of Formula (I) used according to the invention, it is essential that the (meth)acrylamide phosphates are not applied to the filler, as the phosphoric acid groups are bonded by the filler surface in the process.

In addition, the compounds according to the invention can contain further additives, such as e.g. stabilizers, flavours, microbiocidal agents, fluoride ion-releasing additives, optical whitening agents, plasticizers or UV absorbers.

The (meth)acrylamide phosphates of Formula (I) are particularly suitable for the preparation of dental materials, in particular adhesives, coating materials and composites for dental purposes.

The (meth)acrylamide phosphates of Formula (I) are quite particularly suitable for the preparation of dental adhesives and self-adhesive fixing cements, in particular for the preparation of enamel-dentine adhesives. Such adhesives and cements are characterized by a very good adhesion to the hard tooth substance and are hydrolysis-stable under moist conditions.

According to the invention, dental materials which contain the following components are particularly preferred:
a) 0.5 to 95 wt.-%, preferably 10 to 60 wt.-% and particularly preferably 15 to 50 wt.-% (meth)acrylamide phosphate according to Formula (I),
b) 0.01 to 15 wt.-%, particularly preferably 0.1 to 8.0 wt.-% initiator for the radical polymerization,
c) 0 to 80 wt.-%, preferably 0 to 60 wt.-% and particularly preferably 10 to 50 wt.-% non-acid monomer,
d) 0 to 95 wt.-%, preferably 0 to 80 wt.-% and particularly preferably 20 to 60 wt.-% solvent,
e) 0 to 20 wt.-% filler.

The quantity of filler depends particularly on the desired application of the dental material. For the application as adhesive, 0 to 20 wt.-%, and for the application as cement 20 to 75 wt.-%, filler is preferred.

Other additives and adjuvants are optionally used in a quantity of 0.01 to 10 wt.-%.

Unless otherwise indicated all percentages relate to the total mass of the material.

The invention is explained in more detail below with reference to examples.

EMBODIMENTS

Example 1

Phosphoric acid mono-(1-acryloyl-piperidin-4-yl)-ester (APP)

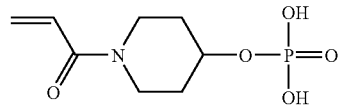

1st Stage: 1-(4-hydroxy-piperidin-1-yl)-propenone 10.11 g (0.10 mol) of 4-hydroxypiperidine was dissolved in 60 ml of 2M NaOH. The solution was stirred at room temperature for 10 minutes and then cooled to 0° C. A solution of 9.96 g (0.11 mol) of acrylic acid chloride and 20 mg of 2,6-di-tert.-butyl-4-methylphenol (BHT) in 60 ml of chloroform was added dropwise within 2 hours at 0° C. After the addition was completed, the clear, yellow reaction mixture was stirred at 0° C. for 1 hour, then the ice bath was removed and the mixture stirred at room temperature for another 3 hours. Organic and aqueous phases were separated. The aqueous phase was saturated with NaCl and extracted with 5×100 ml of chloroform. The combined organic phases were dried over $Na_2SO_4$, filtered, concentrated in a rotary evaporator after addition of 20 mg of BHT and dried in a fine vacuum. The yellowish oil was taken up in 5 ml of ethyl acetate and purified by means of column chromatography (silica gel 60, 0.035-0.070 mm, ethyl acetate). The solvent was concentrated in a rotary evaporator after addition of 25 mg of BHT and dried in a fine vacuum. 4.35 g (28.0 mmol, 28%) of a yellowish oil was obtained which set to form a yellowish solid when stored in a refrigerator.

$^1$H NMR (CDCl$_3$, 400 MHz): δ=1.47-1.63 (m; 2H; CH$_2$), 1-82-1.96 (m; 2H; CH$_2$), 3.22-3.88 (m; 2H; CH$_2$), 3.77-3.88 (m; 1; CH), 3.88-3.98 (m; 2H; CH$_2$), 3.98-4.16 (m; 1; OH), 5.68-5.70 (dd, J=1.7 Hz, 10.8 Hz; 1H; =CH), 6.20-6.24 (dd, J=2.0 Hz, 16.6 Hz; 1H; =CH), 6.56-6.63 (dd, J=10.6 Hz, 16.8 Hz; 1H; =CH).

$^{13}$C NMR (CDCl$_3$, 100 MHz): δ=33.7 (CH$_2$), 34.5 (CH$_2$), 39.5 (CH$_2$), 43.2 (CH$_2$), 66.5 (CH), 127.7 (CH$_2$), 127.8 (CH), 165.5 (C)

2nd Stage: Phosphoric acid(1-acryloyl-piperidin-4-yl) ester-dimethylester 2.60 g (18.0 mmol) of dimethyl chlorophosphate, 2.33 g (15.0 mmol) of 1-(4-hydroxy-piperidin-1-yl)-propenone, 10 mg of hydroquinone monomethyl ether (MEHQ) and 10 mg of BHT were dissolved under argon in 50 ml of dichloromethane and cooled to −5° C. in an ice bath. 2.36 g (21.0 mmol) of potassium-tert.-butylate was added accompanied by stirring. Stirring was carried out for 30 minutes accompanied by cooling in ice, the solution turning a brownish colour, then the ice bath was removed and the mixture stirred at room temperature for 4 hours. 50 ml of a saturated aqueous NH$_4$Cl solution was then added. The mixture was stirred for 10 minutes, then the phases were separated. The aqueous phase was extracted with 2×50 ml of dichloromethane. The combined organic phases were dried over Na$_2$SO$_4$, filtered, concentrated in a rotary evaporator after addition of 20 mg of BHT and dried in a fine vacuum. The brown oil was taken up in 5 ml of dichloromethane and purified by means of column chromatography (silica gel 60, 0.035-0.070 mm, methylene chloride/ethanol 98:2). The eluent was concentrated in a rotary evaporator after addition of 20 mg of BHT and dried in a fine vacuum. 3.02 g (11.5 mmol, 76%) of a red-brown oil was obtained.

| C$_{10}$H$_{18}$NO$_5$P | Calc. | C | 45.63 | H | 6.89 | N | 5.32 |
|---|---|---|---|---|---|---|---|
| (263.23) | Found | | 43.12 | | 7.19 | | 4.96 |

IR: 3475 (w), 2956 (w, C—H), 1642 (s, C═O), 1608 (s, C═C), 1441 (s, C—H), 1366 (w), 1258 (s, P═O), 1219 (m), 1188 (m), 1000 (vs), 893 (m), 847 (s), 791 (m), 766 (m).

$^1$H NMR (CDCl$_3$, 400 MHz): δ=1.73-1.87 (m; 2H; CH$_2$), 1-92-2.03 (m; 2H; CH $_2$), 3.40-3.64 (m; 2H; CH$_2$), 3.78 (d, J=11.1 Hz; 6H; O—CH$_3$), 3.81-3.94 (m; 2H; CH$_2$), 4.59-4.70 (m; 1; CH), 5.59 (dd, J=2.0 Hz, 10.6 Hz; 1H; ═CH), 6.25 (dd, J=2.0 Hz, 16.6 Hz; 1H; ═CH), 6.61 (dd, J=10.6 Hz, 16.9 Hz; 1H; ═CH).

$^{13}$C NMR (CDCl$_3$, 100 MHz): δ=31.8, 32.8 (CH$_2$), 38.6 (CH$_2$), 42.4 (CH$_2$), 54.3, 54.3 (CH$_2$), 73.7, 73.7 (CH), 127.6 (CH), 127.8 (CH$_2$), 165.4 (C)

$^{31}$P NMR (CDCl$_3$, 162 MHz): δ=1.4.

3rd Stage: Phosphoric acid mono-(1-acryloyl-piperidin-4-yl) ester 1.32 g (5.0 mmol) of phosphoric acid dimethyl-[4-(N-acryloyl-piperidyl]ester and 10 mg of BHT were dissolved under argon in 5 ml of dichloromethane. 1.68 g (11.0 mmol) of bromotrimethylsilane was added dropwise. The clear yellowish solution was stirred for 4 hours at room temperature after the addition was completed. For the removal of volatile components, the solution was evacuated at 45° C. for 45 minutes. The oily yellow residue was mixed with 5 ml of methanol. The clear yellowish solution was stirred for 18 hours at room temperature and then concentrated in a rotary evaporator and dried in a fine vacuum. The highly viscous yellowish oil was mixed with 10 ml of dichloromethane and stirred at room temperature. A light yellowish solid formed. This was filtered off and dried in a vacuum drying cabinet. The process was repeated with 18 ml each of ethyl acetate and acetone. The white solid was mixed with 5 ml of i-propanol and stirred at room temperature for 18 hours. The suspension was filtered, and the filtrate was concentrated in a rotary evaporator and dried in a fine vacuum. 0.31 g (1.3 mmol; 26%) of a white solid was obtained.

$^1$H NMR (DMSO-d$_6$, 400 MHz): δ=1.46-1.64 (m; 2H; CH$_2$), 1.77-1.95 (m; 2H; CH$_2$), 3.24-3.47 (m; 2H; CH$_2$), 3.69-3.87 (m; 2H; N—CH$_2$), 4.31-4.43 (m; 1H; O—CH), 5.66 (dd, J=2.5 Hz, 10.5 Hz; 1H; ═CH), 6.09 (dd, J=2.5 Hz, 16.7 Hz; 1H; ═CH), 6.80 (dd, J=10.6 Hz, 16.7 Hz; 1H; ═CH).

$^{31}$P NMR (DMSO-d$_6$, 162 MHz): δ=−0.6.

Example 2

1,3-bis-(N-acryloyl-N-propyl-amino)-propan-2-yl-dihydrogen phosphate (BAPAPP)

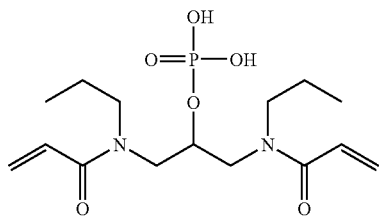

1st Stage: 1,3-bis-(N-acryloyl-N-propyl-amino)-2-hydroxypropane 17.43 g (0.100 mol) of 1,3-bis-(propylamino-propan-2-ol was mixed with 110 ml (0.220 mol) of 2N caustic soda solution and stirred at room temperature for 10 minutes. The mixture was cooled to 0° C. A solution of 19.46 g (0.215 mol) of acrylic acid chloride and 20 mg of BHT in 120 ml of chloroform was added dropwise at 0° C. within 3 hours 30 minutes. After the addition was completed the reaction mixture was stirred at 0° C. for 2 hours 30 minutes. Organic and aqueous phases were separated. The aqueous phase was saturated with NaCl and extracted with 5×80 ml of methylene chloride. The combined organic phases were dried over Na$_2$SO$_4$, filtered, concentrated in a rotary evaporator after addition of 20 mg of BHT and dried in a fine vacuum. The raw product was purified by means of two-fold column chromatography (silica gel 60, 0.035-0.070 mm, ethyl acetate). 11.92 g (42.2 mmol; 42%) of the pure product was obtained as a yellowish oil.

| C$_{15}$H$_{26}$N$_2$O$_3$ | Calc. | C | 63.80 | H | 9.28 | N | 9.92 |
|---|---|---|---|---|---|---|---|
| (282.39) | Found | | 63.54 | | 9.16 | | 9.67 |

IR: 3349 (m, —OH), 2963 (m), 2933 (m), 2875 (m, C—H), 1641 (vs, C═O), 1603 (vs, C═C), 1427 (vs, C—H), 1370 (m, —O—H), 1271 (w), 1229 (s), 1132 (m, —C—OH), 1059 (m), 977 (s), 957 (m), 895 (w), 794 (s), 745 (m).

$^1$H NMR (CDCl$_3$, 400 MHz): δ=0.86-0.93 (m; 6H; CH$_3$), 1.57-1.68 (m; 4H; CH$_2$—CH$_3$), 3.25-3.53 (m; 8H; CH$_2$—N), 4.06-4.09 (m; 1H; CH), 4.96-4.99 (m; 1H; OH), 5.62-5.74 (m; 2H; ═CH), 6.25-6.38 (m; 2H; ═CH), 6.54-7.00 (m; 2H; ═CH).

$^{13}$C NMR (CDCl$_3$, 100 MHz): δ=11.1 (CH$_3$), 11.4 (CH$_3$), 20.6 (CH$_2$), 22.5 (CH$_2$), 22.6 (CH$_2$), 48.8 (CH$_2$), 51.4 (CH$_2$), 51.6 (CH$_2$), 51.9 (CH$_2$), 52.0 (CH$_2$), 70.0 (CH), 71.7 (CH), 127.2 (CH), 127.3 (CH), 127.6 (CH), 128.4 (CH), 128.5 (CH$_2$) 128.7 (CH$_2$), 167.8 (C).

2nd Stage: 1,3-bis-(N-acryloyl-N-propyl-amino)-
propan-2-yl dimethylphosphate 2.60 g (18.0 mmol) of dimethylchlorophosphate, 4.24 g (15.0 mmol) of 1,3-bis-(N-acryloyl-N-propyl-amino)-2-hydroxypropane, 20 mg of MEHQ and 20 mg of BHT were dissolved under argon in 80 ml of dichloromethane and cooled to −5° C. in an ice bath. 2.36 g (21.0 mmol) of potassium-tert.-butylate was added accompanied by stirring. The mixture was ice-cooled and stirred for 30 minutes, the solution turning a slightly yellowish colour, then the ice bath was removed, and the mixture was stirred at room temperature for 4 hours. Then 80 ml of saturated aqueous $NH_4Cl$ solution was added. The mixture was stirred for 10 minutes, then the phases were separated. The aqueous phase was extracted with 2×80 ml of dichloromethane. The combined organic phases were dried over $Na_2SO_4$, filtered, concentrated in a rotary evaporator after addition of 30 mg BHT and dried in a fine vacuum. The raw product was purified by means of column chromatography (silica gel 60, 0.035-0.070 mm), ethyl acetate/acetone 90:10→80:20). 2.74 g (11.6 mmol; 50%) of a yellowish oil was obtained.

3rd Stage: 1,3-bis-(N-acryloyl-N-propyl-amino)-
propan-2-yl dihydrogen phosphate 1.17 g (3.0 mmol) of 1,3-bis-(N-acryloyl-N-propyl-amino)-propan-2-yl dimethylphosphate and 10 mg of BHT were dissolved under argon in 5 ml of dichloromethane. 1.01 g (6.6 mmol) of bromotrimethylsilane was added dropwise. The clear yellowish solution was stirred at room temperature for 3 hours after the addition was completed. In order to remove volatile components the solution was evacuated for 45 minutes at 45° C. The oily yellow residue was mixed with 5 ml of methanol, and the clear yellowish solution was stirred at room temperature for 18 hours. The solution was concentrated in a rotary evaporator and dried in a fine vacuum. 1.21 g (3.3 mmol; 111%) of a slightly yellowish foam was obtained.

Example 3

Examination of the Hydrolysis Stability of the phosphoric acid mono-(1-acryloyl-piperidin-4-yl) ester A 20% solution of the phosphoric acid mono-(1-acryloyl-piperidin-4-yl) ester from Example 1 stabilized with 200 ppm of 2,6-di-t-butyl-4-methylphenol in $D_2O$/EtOH-$d_6$ (1:1) was prepared, this was stored at 37° C. and examined by $^1$H-NMR spectroscopy. After a storage time of 3 months no changes in the $^1$H-NMR spectrum were found.

Example 4

Preparation of a Light-Curing Adhesive Based on (meth)acrylamide phosphates (MAP)

In order to examine dentine adhesion to bovine teeth dentine, adhesives with the following composition were prepared (values in wt.-%)

| MAP [wt.-%] | Comonomers [wt.-%] | $H_2O$ [wt.-%] | Initiator [wt.-%] | Adhesion values [MPa] |
|---|---|---|---|---|
| 14.6 BAPAPP[1] | A[2]: 9.7; B[3]: 2.1; C[4]: 47.6 | 25.0% | 1.0% | 10.7 ± 2.6 |
| 14.3 APP[5] | C: 45.1; D[6]: 9.1; E[7]: 5.3; F[8]: 12.4 | 12.8% | 1.0% | 11.9 ± 5.4 |

[1] BAPAPP = monomer from Example 2
[2] A = [1-(methacryloylamino)propyl]-phosphonic acid
[3] B = 6-(N-acryloylamino)hexan-1-ol
[4] C = N, N'-diethyl-1,3-propylene-bisacrylamide
[5] APP = monomer from Example 1
[6] D = D,L-2-(acryloylamino)succinic acid
[7] E = N-(5-hydroxy-pentyl)methacrylamide
[8] F = Aerosil-$H_2O$ mixture Bovine teeth were embedded in plastic cylinders such that the dentine and the plastic were situated at one level. After grinding of the testpieces, a layer of adhesive of the above formulation was rubbed into the dentine surface with a microbrush for 30 seconds, gently blown with an air blower and lit with an Astralis 7 photopolymerization lamp (Ivoclar Vivadent AG) for 20 seconds. A commercially available dental filling composite (Tetric® Ceram, Ivoclar Vivadent AG) was then applied to the adhesive layer and cured for 40 seconds with the Astralis 7 lamp. The testpieces were then stored in water for 24 hours at 37° C. and the adhesive shear strength measured in accordance with the ISO guideline "ISO 1994-ISO TR 11405: Dental Materials Guidance on Testing of Adhesion to Tooth Structure".

The invention claimed is:
1. Polymerizable dental material, which contains the following components:
   a) 0.5 to 95 wt.-% (meth)acrylamide phosphate according to Formula (I):

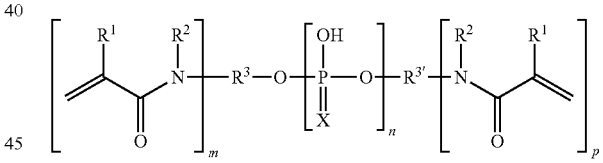

Formula I in which
   $R^1$ is H or $CH_3$;
   $R^2$ forms together with the nitrogen atom to which it is bonded and one or more atoms which belong to $R^3$ or $R^{3'}$ a heterocyclic ring;
   $R^3$, $R^{3'}$ independently of each other are a linear or branched aliphatic $C_1$-$C_{50}$ radical with a valency of m+n or p+n, an aromatic $C_6$-$C_{18}$ radical with a valency of m+n or p+n, or a cycloaliphatic, araliphatic or heterocyclic $C_3$-$C_{13}$ radical with a valency of m+n or p+n, wherein the carbon chains of the radical or radicals can be interrupted by O, S, $CONR^4$, OCONH, or form together with one or more atoms which belong to $R^2$ and the nitrogen atom to which $R^2$ is bonded a heterocyclic ring, $R^{3'}$ being H if p =0, and wherein
   $R^4$ is H, $C_1$-$C_{10}$ alkyl, $C_6$-$C_{12}$ aryl, $C_6$-$C_{10}$ aralkyl or a bicyclic $C_4$-$C_{12}$ radical;
   n is 1, 2, 3 or 4 if p=0, and
   is 1 or 2 if p≠0;
   m is 1, 2, 3 or 4;

p is 0, 1, 2, 3 or 4;
x is 0 or S;
b) 0.01 to 15 wt.-% initiator,
c) 0 to 80 wt.-% non-acid radically polymerizable monomer,
d) 0 to 95 wt.-% solvent, and
e) 0 to 20 wt.-% filler,
said dental material having a pH of about 0.5 to 3.0, and being capable of etching a tooth substance,
wherein the $R^2$ heterocyclic ring is a ring with one nitrogen atom and 4 to 7 carbon atoms.

2. Dental material according to claim 1, which additionally contains a solvent.

3. Dental material according to claim 2, which contains as solvent water or a mixture of water and a solvent miscible with water.

4. Dental material according to claim 1, which additionally contains at least one non-acid, radically polymerizable monomer.

5. Dental material according to claim 4, which contains as non-acid monomer one or more monomers from the following group: mono(meth)acryl compounds, mesityl(meth)acrylate, 2-(alkoxymethyl)acrylic acids, 2-(ethoxymethyl)acrylic acid, 2-(hydroxymethyl)acrylic acid, N-mono and N-disubstituted acrylamides, N-ethylacrylamide, N,N-dimethylacrylamide, N-(2-hydroxyethyl)acrylamide, N-methyl-N-(2-hydroxyethyl) acrylamide, N-monosubstituted methacrylamide, N-ethylmethacryl amide, N-(2-hydroxyethyl) methacrylamide, N-vinylpyrrolidone and allyl ethers.

6. Dental material according to claim 4, which contains as non-acid monomer one or more monomers from the following group: urethanes from 2-(hydroxymethyl) acrylic acid and diisocyanates, 2,2,4-trimethylhexamethylene diisocyanate, isophorone diisocyanate, cross-linking pyrrolidones, 1,6-bis (3-vinyl-2-pyrrolidonyl) -hexane, bisacrylamides, methylene and ethylene bisacrylamide, bis(meth)acrylamides, N,N'-diethyl-1,3-bis(acrylamido)-propane, 1,3-bis(methacrylamido)-propane, 1,4-bis(acrylamido)-butane and 1,4-bis(acryloyl)-piperazine.

7. Dental material according to claim 1, which contains up to 20 wt. % of at least one filler and wherein the (meth)acrylamide phosphate of formula (I) is not applied to the surface of the filler.

8. Dental material according to claim 1, which additionally contains
f) 0.01 to 10 wt.-% of one or more further additives.

9. Dental material according to claim 1, wherein the heterocyclic ring is a piperidinyl ring.

10. Polymerizable dental material, which contains the following components:
a) 0.5 to 95 wt.-% (meth)acrylamide phosphate according to Formula (I):

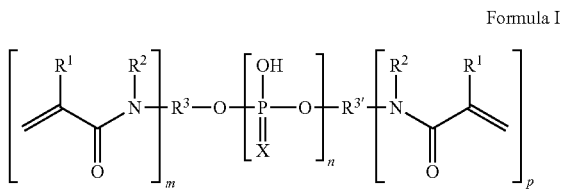

Formula I in which
$R^1$ is H or $CH_3$;
$R^2$ forms together with the nitrogen atom to which it is bonded and one or more atoms which belong to $R^3$ or $R^{3'}$ a heterocyclic ring;
$R^3$, $R^{3'}$ independently of each other are a linear or branched aliphatic $C_1$-$C_{50}$ radical with a valency of m+n or p+n, an aromatic $C_6$-$C_{18}$ radical with a valency of m+n or p+n, or a cycloaliphatic, araliphatic or heterocyclic $C_3$-$C_{13}$ radical with a valency of m+n or p+n, wherein the carbon chains of the radical or radicals can be interrupted by O, S, $CONR^4$, OCONH, or form together with one or more atoms which belong to $R^2$ and the nitrogen atom to which $R^2$ is bonded a heterocyclic ring, $R^{3'}$ being H if p =0, and
wherein
$R^4$ is H, $C_1$-$C_{10}$ alkyl, $C_6$-$C_{12}$ aryl, $C_6$-$C_{10}$ aralkyl or a bicylic $C_4$-$C_{12}$ radical;
n is 1, 2, 3 or 4 if p=0, and is 1 or 2 if p≠0;
m is 1, 2, 3 or 4;
p is 0, 1, 2, 3 or 4;
x is 0 or S;
b) 0.01 to 15 wt.-% initiator,
c) 0 to 80 wt.-% non-acid radically polymerizable monomer,
d) 0 to 95 wt.-% solvent, and
e) 0 to 20 wt.-% filler,
said dental material having a pH of about 0.5 to 3.0, and being capable of etching a tooth substance,
wherein the $R^3$ heterocyclic ring is a ring with one nitrogen atom and 4 to 7 carbon atoms.

11. Dental material according to claim 10, wherein the heterocyclic ring is a piperidinyl ring.

* * * * *

UNITED STATES PATENT AND TRADEMARK OFFICE
CERTIFICATE OF CORRECTION

| | | |
|---|---|---|
| PATENT NO. | : 7,622,538 B2 | Page 1 of 1 |
| APPLICATION NO. | : 11/211938 | |
| DATED | : November 24, 2009 | |
| INVENTOR(S) | : Moszner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this

Twenty-sixth Day of October, 2010

David J. Kappos
*Director of the United States Patent and Trademark Office*